US007228302B2

(12) United States Patent
Kuchinsky et al.

(10) Patent No.: US 7,228,302 B2
(45) Date of Patent: Jun. 5, 2007

(54) SYSTEM, TOOLS AND METHODS FOR VIEWING TEXTUAL DOCUMENTS, EXTRACTING KNOWLEDGE THEREFROM AND CONVERTING THE KNOWLEDGE INTO OTHER FORMS OF REPRESENTATION OF THE KNOWLEDGE

(75) Inventors: Allan J. Kuchinsky, San Francisco, CA (US); Aditya Vailaya, Santa Clara, CA (US); David Moh, San Francisco, CA (US); Peter Bluvas, Amsterdam, NY (US)

(73) Assignee: Agilent Technologies, Inc., Santa Clara, CA (US)

( * ) Notice: Subject to any disclaimer, the term of this patent is extended or adjusted under 35 U.S.C. 154(b) by 527 days.

(21) Appl. No.: 10/642,376

(22) Filed: Aug. 14, 2003

(65) Prior Publication Data

US 2005/0038770 A1    Feb. 17, 2005

(51) Int. Cl.
*G06F 7/00* (2006.01)
*G06F 17/30* (2006.01)
(52) U.S. Cl. ......................... 707/6; 707/102
(58) Field of Classification Search ............. 707/1–10, 707/100–104.1, 200–205
See application file for complete search history.

(56) References Cited

U.S. PATENT DOCUMENTS

| | | | | |
|---|---|---|---|---|
| 6,067,552 | A * | 5/2000 | Yu ........................... | 715/501.1 |
| 6,292,830 | B1 * | 9/2001 | Taylor et al. ............... | 709/224 |
| 6,332,138 | B1 * | 12/2001 | Hull et al. ..................... | 707/5 |
| 6,496,832 | B2 | 12/2002 | Chi et al. | |
| 6,745,204 | B1 * | 6/2004 | Hogue et al. ............ | 707/104.1 |
| 2002/0178184 | A1 | 11/2002 | Kuchinsky et al. | |

FOREIGN PATENT DOCUMENTS

EP    1 260 918  A2    11/2002

OTHER PUBLICATIONS

Pending U.S. Appl. No. 10/033,823, filed Dec. 19, 2001.
Pending U.S. Appl. No. 10/154,529, filed May 22, 2002.
Pending U.S. Appl. No. 10/155,675, filed May 22, 2002.
Pending U.S. Appl. No. 10/155,405, filed May 22, 2002.
Pending U.S. Appl. No. 10/155,304, field May 22, 2002.
Pending U.S. Appl. No. 10/555,616, filed May 22, 2002.
Pending U.S. Appl. No. 10/154,524, filed May 22, 2002.
Pending U.S. Appl. No. 10/641,492, filed Aug. 14, 2003.
Chi et al., "A Spreadsheet Approach to Information Visualization", not dated.
Dahlquist et al., "GenMAPP, a new tool for viewing and analyzing microarray data on biological pathways", nature genetics, vol. 31, May 2002.
Doniger et al., "MAPPFinder: using Gene Ontology and GenMAPP to create a global gene-expression profile from microarray data", Genome Biology 2003, vol. 4, Issue 1, Article R7.
Wolf et al., "Case Study: Visualising gene expression in its metabolic context", Henry Stewart Publications, 1467-5463, Briefings in Bioinformatics, vol. 1, No. 3, 297-304, Sep. 2000.

(Continued)

*Primary Examiner*—Hosain Alam
*Assistant Examiner*—Navneet K. Ahluwalia

(57) ABSTRACT

Systems, tools, methods and recordable media for text mining textual documents and extracting and associating entities and interactions mined with other data formats, such as diagrammatic displays and experimental data, using a local format. Additionally, information may be overlaid and compared with existing biological diagrams.

65 Claims, 9 Drawing Sheets

OTHER PUBLICATIONS

Marti A. Hurst, "Untangling Test Data Mining", Proceedings of ACL '99: The 37th Annual Meeting of the Association for Computational Linguistics, Jun. 20, 1999 - Jun. 26, 199 Retrieved from the Internet XP002400582.

Aditya Vallaya, et al., "An Architecture for Biological Information Extraction and Representation", 2004 ACM Symposium on Applied Computing, Mar. 14, 2004 - Mar. 17, 2004; pp. 103-110, XP002400583.

Kamal Kumar, et al., BioMap: Toward the Development of a Knowledge Base of Biomedical Literature; 2004 ACM Symposium on Applied Computing, Feb. 14, 2004 - Mar. 17, 2004, pp. 121-127, XP002400584.

Carol Friedman, et al., "GENIES: a natural-language processing system for the extraction of molecular pathways from journal articles", BioInformatics, Oxford University Press, Oxford, GB., vol. 17, No. 1, 2001, pp. 74-82, XP002391342.

Michael Krauthammer, et al., "Of truth and pathways: chasing bits of information through myriads of articles", BioInformatics, Oxford Press, Oxford, GB., vol. 18, No. 1, 2002, pp. S249-S257, XP002391342.

Zhengxin Chen, et al., Query construction of user-guided knowledge discovery in databases, Information Sciences, Amsterdam, NL vol. 109, No. 1-4, Aug. 1998, pp. 49-64, XP005479943.

* cited by examiner

SYSTEM, TOOLS AND METHODS FOR VIEWING TEXTUAL DOCUMENTS, EXTRACTING KNOWLEDGE THEREFROM AND CONVERTING THE KNOWLEDGE INTO OTHER FORMS OF REPRESENTATION OF THE KNOWLEDGE

FIELD OF THE INVENTION

The present invention pertains to the field of biological data management. More particularly, the present invention relates to identifying and interrelating biological information contained within textual documents with other types of data, such as biological diagrams and experimental data, and using such information interactively with biological diagrams.

BACKGROUND OF THE INVENTION

The advent of high-throughput experimental technologies for molecular biology have resulted in an explosion of data and a rapidly increasing diversity of biological measurement data types. Examples of such biological measurement types include gene expression from DNA microarray or Quantitative PCR experiments, protein identification from mass spectrometry or gel electrophoresis, cell localization information from flow cytometry, phenotype information from clinical data or knockout experiments, genotype information from association studies and DNA microarray experiments, etc. This data is rapidly changing; new technologies frequently generate new types of data. In addition to data from their own experiments, biologists also utilize a rich body of available information from Internet-based sources, e.g. genomic and proteomic databases, and from the scientific literature. The structure and content of these sources is also rapidly evolving. The software tools used by molecular biologists need to gracefully accommodate new and rapidly changing data types.

One manner in which biologists use these experimental data and other sources of information is in an effort to piece together interpretations and form hypotheses about biological processes, also referred to as building biological models. Textual documents are often relied upon as a source of "known" information, which can be used to compare to experimental data and/or in constructing biological diagrams/models, to confirm or refute hypotheses or data resulting from experimentation for example.

A large number of systems have been developed to automatically build biological models from these various sources of biological data. However, these tools suffer from at least two major limitations: they lack accuracy in extracting knowledge for building the biological models, and also, they cannot incorporate a user's changing contexts and hence are not true to users' intents. Manual building of models has the strength that the model is true to the user's intent. By manually building, the model builder can capture all the nuances and subtleties that only a human can provide. There are significant disadvantages in manually building such models, however, in that the process of building biological models is tedious and error prone, particularly as data and models get larger and more complex.

Likewise, manual extraction of knowledge from text has the advantage that the extractions made are each individually chosen by the user and therefore only relevant data is generally extracted by this method. Again, however, this method is extremely tedious, time-consuming, and inefficient.

There are currently systems that can generate biological network information, such as protein-protein interaction networks, via knowledge extraction from text, and which display their output via network diagrams. Examples of these are Ariadne Genomics (www.ariadnegenomics.com); Apelon (www.apelon.com), BioSentients (www.biosentients.com); BioWisdom (www.biowisdom.co.uk); Cellomics CellSpace™ (http://www.cellomics.com/products/cellsace/); Definiens (www.definiens.de); Gene Ed/Reel Two (www.geneed.com www.reeltwo.com); Incellico (www.incellico.com); Ingenuity (www.ingenuity.com); Insightful (www.insightful.com); Iridescent (http://innovation-.swmed.edu./Biocomnputing/Computing.htm); Pre-BIND (http://www.binddb.org); PubGene (http://www.pubgene.com/); Virtual Genetics (www.vglab.com); and XMine (htt://www.x-mine.com/). These systems rely on statistical and linguistic natural language processing to automatically pre-compute protein-protein interactions from scientific text into a database. They therefore present a completely generated network to the user; there is no opportunity for the user to guide and/or improve the process of knowledge extraction by disambiguating and/or assigning directionality or causality. These systems are also plagued by numerous inaccuracies and inconsistencies, leading to skepticism by would-be users in real practice.

In view of the existing systems, what is needed are systems methods and tools capable of not only easily and semi-automafically (i.e., providing the opportunity for user input and/or editing) extracting knowledge or relevant information from textual documents, but which also provide for user interaction to guide and improve the resultant information that is extracted, such as by error correction, disambiguation, and/or custom tailoring to the user's needs.

SUMMARY OF THE INVENTION

The present invention provides systems, methods and computer readable media for manipulating biological data. The present invention provides tools to convert free-form information in scientific text to a structured, machine readable format, such as the local format, which can then be used to link various forms of biological data for their interactive use.

The present invention provides systems, tools and methods for providing interactive capabilities for user involvement in extracting and disambiguating biological information in scientific text to be converted into a structured format, such as the local format. The local format can then be used in generating a biological diagram. For example, one such tool provides a text viewer into which at least a portion of a textual document may be imported and viewed; means for text mining the text having been imported into the text viewer; a list-based text editor that lists entities and interactions having been identified by the text mining; and means for assigning directionality to the listed interactions.

The entities and interactions listed each point back to a location of the portion of the textual document where it was identified. Slots are associated with each interaction listed so that a user can identify one or more of the listed entities involved in the interaction, and assign the roles played by each of these entities, in a particular interaction.

A canvas area may be provided for diagrammatically representing entities and interactions having been identified by text mining, or biological diagrams may be generated based on identified entities and interactions and displayed on a separate graphical viewer. At least one pre-designed blank graphical rendering representing a particular type of interaction may be provided for use in population thereof in the canvas area. Population may be with one or more of entities and interactions identified during text mining of a textual document.

User context may be provided to process scientific text to identify entities and interactions within the textual document.

Textual documents may be processed in batch mode, including any and all of the steps of textual searching to identify relevant documents, identification and local formatting of entities and interactions within textual documents; disambiguation of interactions that have been identified, highlighting of locations of identified entities and/or interactions in the textual documents where they were extracted, construction of one or more biological diagrams using identified entities and interactions, and alias management of alias names for entities and/or interactions.

A tool for building biological networks of interactions is provided, which includes a text viewer, means for text mining, a list-based text editor, means for assigning directionality to the listed interactions or additionally converting interactions into a local format; and means for selecting interactions and associated entities in the list-based editor, merging common entities and displaying a resulting network of the interactions in the network viewer.

A tool for comparing extracted biological knowledge against an existing biological diagram is provided, including a text viewer, means for text mining, a list-based text editor, a diagram viewer and means for importing at least a portion of an existing biological diagram into the diagram viewer; means for overlaying the identified entities and interactions on the existing biological diagram that is displayed in the diagram viewer, and means for visually distinguishing the overlaid entities and interactions from a remainder of the displayed biological diagram.

By use of the present invention, a user may easily and conveniently construct diagrammatic representations of data/text that can be used to make an interactive biological diagram.

A user context is provided as a basis upon which text mining and other related functions of the present system function. The user context may be readily edited by a user. The user context may be created by the user or a new user context can be created to replace an existing context.

Alias management functionality is provided so that functions may be run concurrently with regard to an entity (concept) and/or interaction (relationship), as well as any known existing aliases.

Batch mode processing of textual documents is also provided.

Methods for using each of the above tools and systems, either alone or in any usable combination are also provided.

These and other advantages and features of the invention will become apparent to those persons skilled in the art upon reading the details of the invention as more fully described below.

BRIEF DESCRIPTION OF THE DRAWINGS

FIG. 6B shows detail from a pane in FIG. 6A.

DETAILED DESCRIPTION OF THE INVENTION

Figure 1:
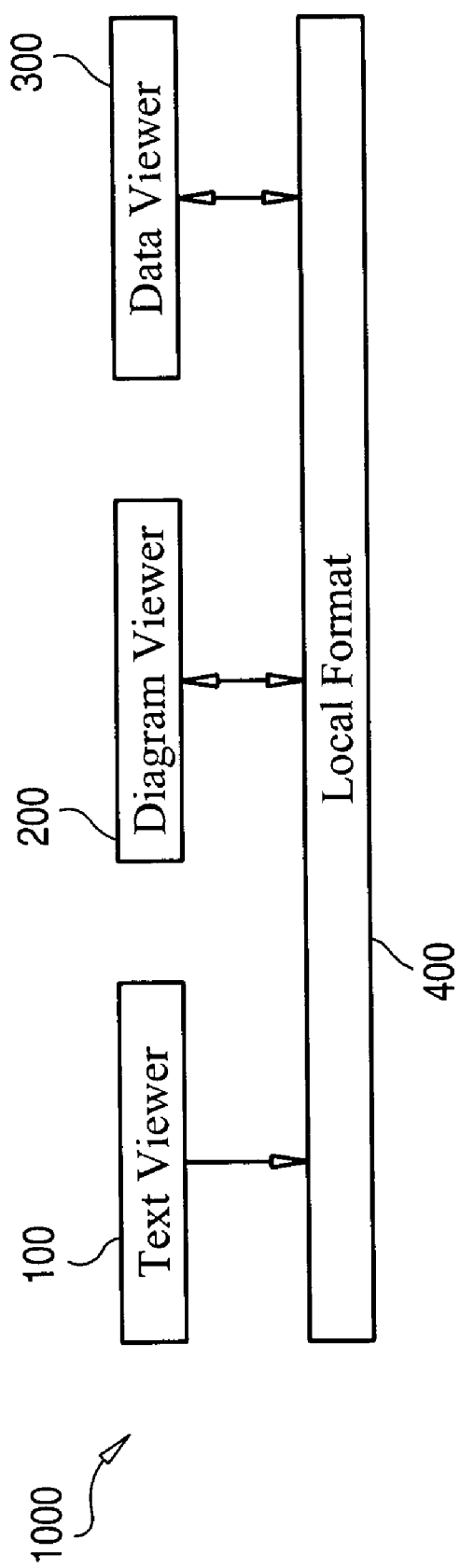
FIG. 1 is a schematic representation of a system for facilitating interaction, comparisons, overlays, etc. of information from different categories, such as textual material (e.g., scientific literature), experimental data and biological diagrams.

Before the present systems, tools and methods are described, it is to be understood that this invention is not limited to particular software, hardware, software language or symbols described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a concept" includes a plurality of such concepts and reference to "the diagram" includes reference to one or more diagrams and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the present application, unless a contrary intention appears, the following terms refer to the indicated characteristics.

The term "biological diagram" or "biological model", as used herein, refers to any graphical image, stored in ay type of format (e.g., GIF, JPG, TIFF, BMP, etc.) which contains depictions of concepts found in biology. Biological diagrams include, but are not limited to, pathway diagrams, cellular networks, signal transduction pathways, regulatory pathways, metabolic pathways, protein-protein interactions, interactions between molecules, compounds, or drugs, and the like.

A "biological concept" refers to any concept from the biological domain that can be described using one or more "nouns" according to the techniques described herein.

An "entity" or "item" is defined herein as a subject of interest that a researcher is endeavoring to learn more about, and may also be referred to as a biological concept, i.e., "entities" are a subset of "concepts". For example, an entity or item may be one or more genes, proteins, molecules, ligands, diseases, drugs or other compounds, textual or other semantic description of the foregoing, or combinations of any or all of the foregoing, but is not limited to these specific examples.

An "interaction" as used herein, refers to some association relating two or more entities. Co-occurrence of entities in an interaction implies that there exists some relationship between those entities. Entities may play a number of roles within an interaction. The structure of roles in an interaction determines the nature of the relationship(s) amongst the various entities that fill those roles. An empty role in an interaction can be referred to as a "slot" or placeholder, where an entity may be assigned.

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

"May" means optionally.

Methods recited herein may be carried out in any order of the recited events which is logically possible, as well as the recited order of events.

"Local format" refers to a restricted grammar/language used to represent extracted semantic information from diagrams, text, experimental data, etc., so that all of the extracted information is in the same format and may be easily exchanged and used in together. The local format can be used to link information from diverse categories, and this may be carried out automatically. The information that results in the local format can then be used as a precursor for application tools provided to compare experimental data with existing textual data and biological models, as well as with any textual data or biological models that the user may supply, for example.

A "node" as used herein, refers to an entity, which also may be referred to as a "noun" (in a local format, for example). Thus, when data is converted to a local format according to the present invention, nodes are selected as the "nouns" for the local format to build a grammar, language or Boolean logic.

A "link" as used herein, refers to a relationship or action that occurs between entities or nodes (nouns) and may also be referred to as a "verb" (in a local format, for example). Verbs are identified for use in the local format to construct a grammar, language or Boolean logic. Examples of verbs, but not limited to these, include upregulation, downregulation, inhibition, promotion, bind, cleave and status of genes, protein-protein interactions, drug actions and reactions, etc.

Although it is currently possible to identify interactions between biological entities from textual documents, for example, using automated text mining tools, (e.g., it is possible to identify the "nouns" and "verbs" used in describing an interaction involving entities), it was not heretofore possible to unambiguously identify causality or directionality of the interactions. A method and system for knowledge extraction is described in co-pending commonly owned application Ser. No. 10/154,524 titled "System and Method for Extracting Pre-Existing Data from Multiple Formats and Representing Data in a Common Format for Making Overlays", filed on May 22, 2002. application Ser. No. 10/154,524 is hereby incorporated by reference herein, in its entirety, by reference thereto. Further, a method and system for using local user context to extract relevant knowledge is described in co-pending and commonly assigned application Ser. No. 10/155,304 filed May 22, 2002 and titled "System, Tools and Methods to Facilitate Identification and Organization of New Information Based on Context of User's Existing Information". application Ser. No. 10/155,304 is hereby incorporated by reference herein, in its entirety, by reference thereto. Described are methods and systems wherein automated text mining techniques are used to extract "nouns" (e.g. biological entities) and "verbs" (e.g. relationships) from sentences in scientific text. Thus, knowledge extraction from scientific literature, e.g. via text mining, can identify biological entities that are involved in a relationship, for example a promotion interaction involving two genes. The resulting interpretation is represented in a restricted grammar, referred to as "local format".

The present invention converts text to the local format using an interactive text viewing tool. This tool can automatically identify and extract entities and relationships found in a passage of text, and then provide an interface by which a user can interactively refine and disambiguate the extracted knowledge, which the present invention converts to a local format, thereby greatly improving the accuracy and reliability of the knowledge generated, as a result of the process. The local format serves as a structured way for the user to review and encode the relevant knowledge contained in scientific text. It also serves as a biological object model that can be manipulated by other computational tools.

The present invention extends the functionality and versatility of the local format by augmenting automated tools to enable the user to interact with the knowledge extraction process to clarify and/or correct the results of the process by disambiguation, and hence, transform free-form text into the structured representation of the local format. The present invention sits on top of the local format infrastructure and provides an interface by which a user can create local format objects and/or modify existing local format objects. The present invention allows associations to be made between local format objects and entities, concepts, interactions and/or relationships described in textual data, and provides various interfaces which facilitate a user's manipulation of such data as well as the underlying local format objects.

FIG. 1 is a schematic representation of a system 1000 for facilitating interaction, comparisons, overlays, etc. of information from different categories, such as textual material (e.g., scientific literature), experimental data and biological diagrams. Using a local format infrastructure layer 400 (as described in co-pending application Ser. No. 10/154,524 for example, knowledge from one representation (text, data or graphical) may be transformed or linked to one or more other of the representations. This allows combining knowledge from different representations for comparison purposes, for constructing new and more detailed representations of knowledge, and the like. At the local format level 400 the knowledge is converted to a canonical or abstract representation.

This abstract representation serves as a common language (local format) which can be used for textual representations, data representations and graphical representations of knowledge.

While many different textual editors or viewers may be used to access textual representations of knowledge and input such knowledge for conversion to the local format (some may also even data mine and automatically extract nouns and verbs, as noted above), textual viewer 100, according to the present invention, provides for further user interaction for improvement of the knowledge gathered, as well as improvement of the accuracy when converting such knowledge to a local format.

A diagram viewer 200 may be used to view biological diagrams, import graphical knowledge from the same and convert it to the local format at 400 for use with text and/or data. Further special features for conversion of biological diagrams, as well as construction of biological diagrams, which may be accompanied with use of the local format can be found in co-pending, commonly owned application Ser. No. 10/641,492 filed on even date herewith, and titled "Method and System for Data Overlay and Navigation on a Biological Diagram". Application Ser. No. 10/641,492 is incorporated herein, in its entirety, by reference thereto.

Experimental data may be imported and converted to the local format, using a data viewer 300, for overlays on textual documents, biological diagrams, or incorporation of such knowledge with textual knowledge and/or graphical knowledge, through conversion of all types to a local format. However a specific data viewer having functionality analogous to that of the text viewer 100 according to the present invention, or to the functionality of the diagram viewer described in application Ser. No. 10/641,492, has not yet been developed, as the complexities in addressing specific requirements for forming relationships among individual data points and disambiguating such relationships is much more challenging than the tasks presented by either textual knowledge or diagram knowledge.

Thus, the infrastructure layer 400 provides the means/data model by which knowledge from different sources may be converted and displayed at various endpoints (applications) such as text viewer 100, diagram viewer 200 and data viewer 300.

Figure 2:
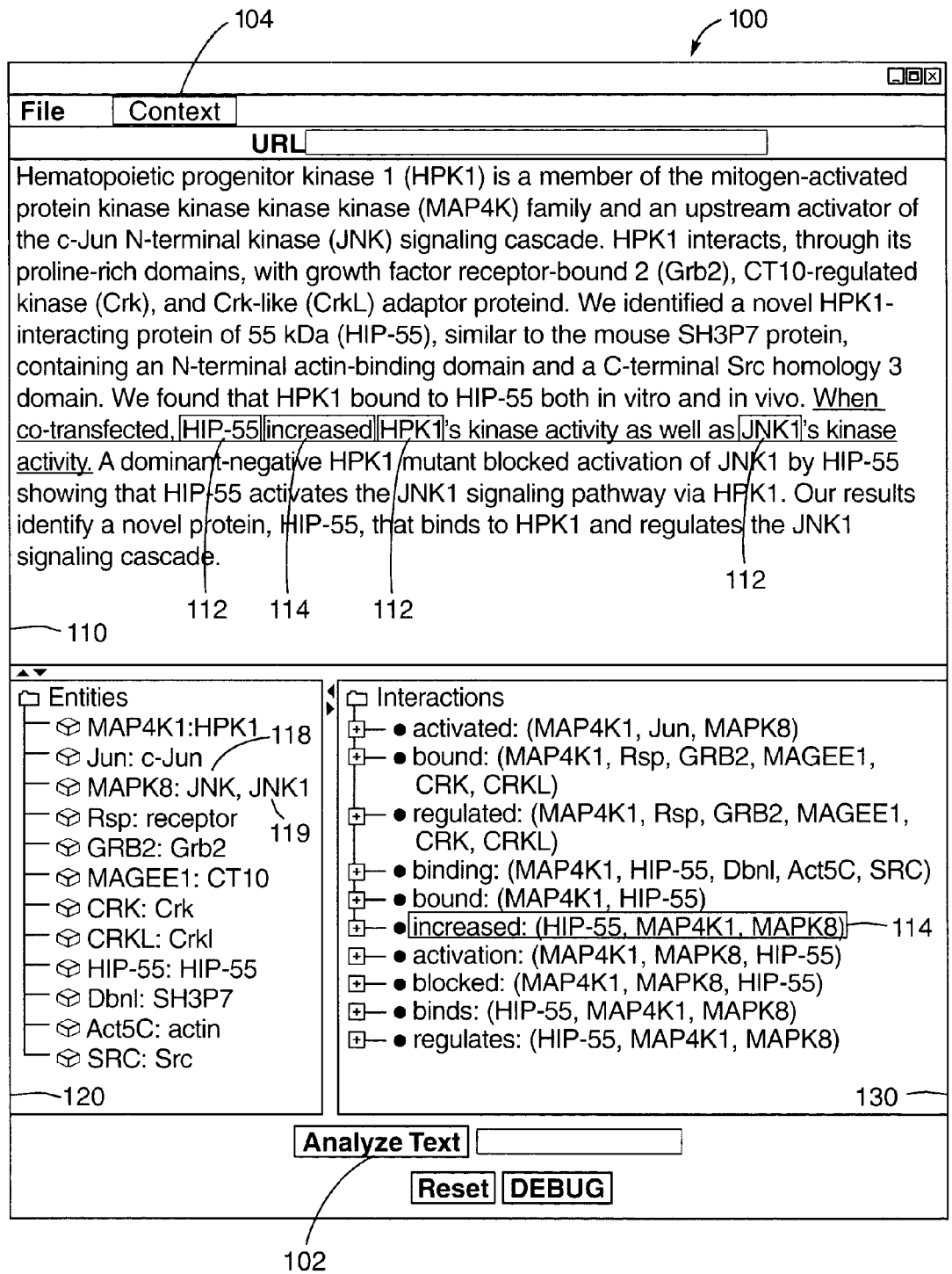
FIG. 2 shows a screen shot of an example of a text viewer tool according to the present invention.

FIG. 2 shows a screen shot of an example of a tool (textual viewer) 100 according to the present invention, which allows a user to extract knowledge from textual forms of biological knowledge. Viewer 100 is configured to involve a user in the process of disambiguation. Tool 100 includes a list-based text editor that allows users to make textual assignments for the entities and interactions identified in a textual document by filling in textual slots or areas of the viewer 100 provided for user input. In the example shown, an excerpt from a publication identified in PubMed (http://www.ncbi.nlm.nih.gov/entrez/query.fcgi?db=PubMed) was inputted into the text viewer window 110 of tool 100, such as by automatic extraction or cutting and pasting, for example. Upon selection of the "Analyze Text" button 102, tool 100 uses the user context and local format tools and methods described in application Ser. Nos. 10/154,524 and 10/155,304 to identify the nouns and verbs contained within the textual excerpt, extract them, and list them in the entities window 120 and interactions window 130, as shown. Each item in the list structure for interactions 130 is a visual representation of the underlying local format, restricted grammar representation of that interaction.

Automated analysis using lexicons for entities and interactions are used to identify the interesting (e.g., those nouns and verbs matching those in the user context or matched by a lookup service for aliases, such as Biological Naming System) nouns and verbs in every sentence of the text. The lexicons are part of the user context provided by tool 100. The lexicons can be set, edited and manipulated by the user when selecting the "Context" menu button 104. For example, creation and/or management/editing of the user context can be preformed by a user with various options. One option is where the user selects specific entities and/or interactions to be inserted into the user context. Another option is to select local format objects (e.g., such as those describing entities and/or interactions) to be inputted and entered in the user context. Still another option is to select all or a portion of an existing biological diagram, convert the entities and interactions in such selection and enter the local format objects resulting from such conversion into the user context. Similarly, a user may create his/her own biological diagram, by freehand sketching or otherwise, convert it to local format objects and use these local format objects in the user context.

Simple rules are applied to break down the text into sentences. The identified nouns are represented in the "Entities" list 120, while the verbs are represented in the "Interactions" list 130, as noted above. A description of an example procedure employing simple rules follows. First the entire text is searched for the occurrence of a period, ".". Then each of these occurrences is examined to throw away cases where the period character is not being used in the text to indicate the end of a sentence. An example of another use for this character is as a decimal point in a number.

For each sentence thus identified, the present invention searches that sentence for the presence of nouns specified in the user context. The present invention is able to recognize different grammatical forms of these nouns, such as plurals, even if they are not explicitly given in a user context. For each noun thus identified, the present invention creates an entity object. All known aliases for a noun, as specified by the user context, are recognized by the present invention as well. These aliases are all mapped to the appropriate single entity object. The location of the noun or one of its aliases within the text is also stored within the entity object according to the present invention. Optionally, a type may be assigned to the entity object, if such information is available in the user context entry for the noun from which the entity was created. If no type is available in user context, the present invention may assign a default type such as 'unknown' or it may attempt to compute a type based upon information which may include metadata about the text source which is being analyzed, other words which occur in the current sentence, or root words of known entities which occur as substrings in the name of the present entity. As more sentences are considered by the current invention, entities are not duplicated, that is, a user context specified noun or an alias which occurs in two separate sentences will be mapped to the same single entity object by the present invention.

Additionally, the present invention breaks down each sentence into individual words. Each of these possible words is first looked up in a dictionary of common English words. This dictionary was created from the dictionary available in the UNIX operating system. The system also stems the words in the dictionary to map different grammatical forms of the same word into one. For example, stemming maps both "proteins" and "protein" to the same stem "protein". Words that are not present in this dictionary are processed further as potential entities. These words are then looked up in a biological naming database. An example of such a database is BNS (Biological Naming System, see U.S. patent application Ser. No. 10/154,529). For each occurrence of a word in such a database, an entity object is created by the present invention. Aliases of database words are recognized in the present invention as well and all known aliases for a single word are mapped to the appropriate single entity object.

For each sentence thus identified, the present invention also searches that sentence for the presence of verbs specified in the user context. The present invention is able to recognize different grammatical forms of these verbs, such as different tenses, even if these different forms are not explicitly given in a user context entry. For each verb thus identified, the present invention creates an interaction object. Additionally, the present invention assigns all other entities which occur in the same sentence as the present verb to unassigned roles in the current interaction. The location of the verb within the text is also stored within the interaction object according to the present invention. Optionally, a type may be assigned to the interaction object, if such information is available in the user context entry for the verb from which the interaction was created. If no type is available in user context, the present invention may assign a default type such as 'unknown' or it may attempt to compute a type based upon information which may include metadata about the text source which is being analyzed, other words which occur in the current sentence, or root words of known Interactions which occur as substrings in the name of the present interaction.

The identified nouns are represented in the "Entities" list 120, while the verbs are represented in the "Interactions" list 130, as noted above. The present invention may display any available information about each Entity or Interaction in the label or icon of its representation in these list-based viewers. For example, the name and known aliases for an entity may be displayed. For an interaction, the name of that interaction along with the names of the entities contained in the interaction may be displayed. Furthermore, a textual representation of the roles played by the entities in that interaction may also be displayed at the interaction's label in the list-based viewer. An example list of roles an entity can play in an interaction includes, but not limited to, affecter, affected, unassigned, unknown, and mediator. In the current system, we have used the affecter, affected, and unassigned roles. However, unknown and mediator roles can also be assigned when a user doesn't know the actual role an entity plays or if the entity plays a mediator role and not the affecter or affected roles, respectively. An example of displaying the roles of entities in an interaction includes, unassigned entities may be displayed in parentheses, while affecter and affected entities may be displayed on the left hand side and right hand side of an arrow, respectively. The present invention may also optionally use a coloring scheme to represent the labels for the entries in these list-based viewers. For example, each unique type of entity or interaction can be assigned to a particular color. The text for the labels of the entities and interactions displayed in these list-based viewers may be rendered in the color corresponding to the type of that entity or interaction. Further, the system allows the user to edit the aliases and names of the identified entities and interactions if some of the information is incorrect. The user can click the right mouse button and a list of action options is shown to the user. One of the options is an "Edit" option, that allows the user to edit the object (entity or interaction). Thus, any errors made by the automatic alias management routines may be manually corrected by the user.

Figure 3:
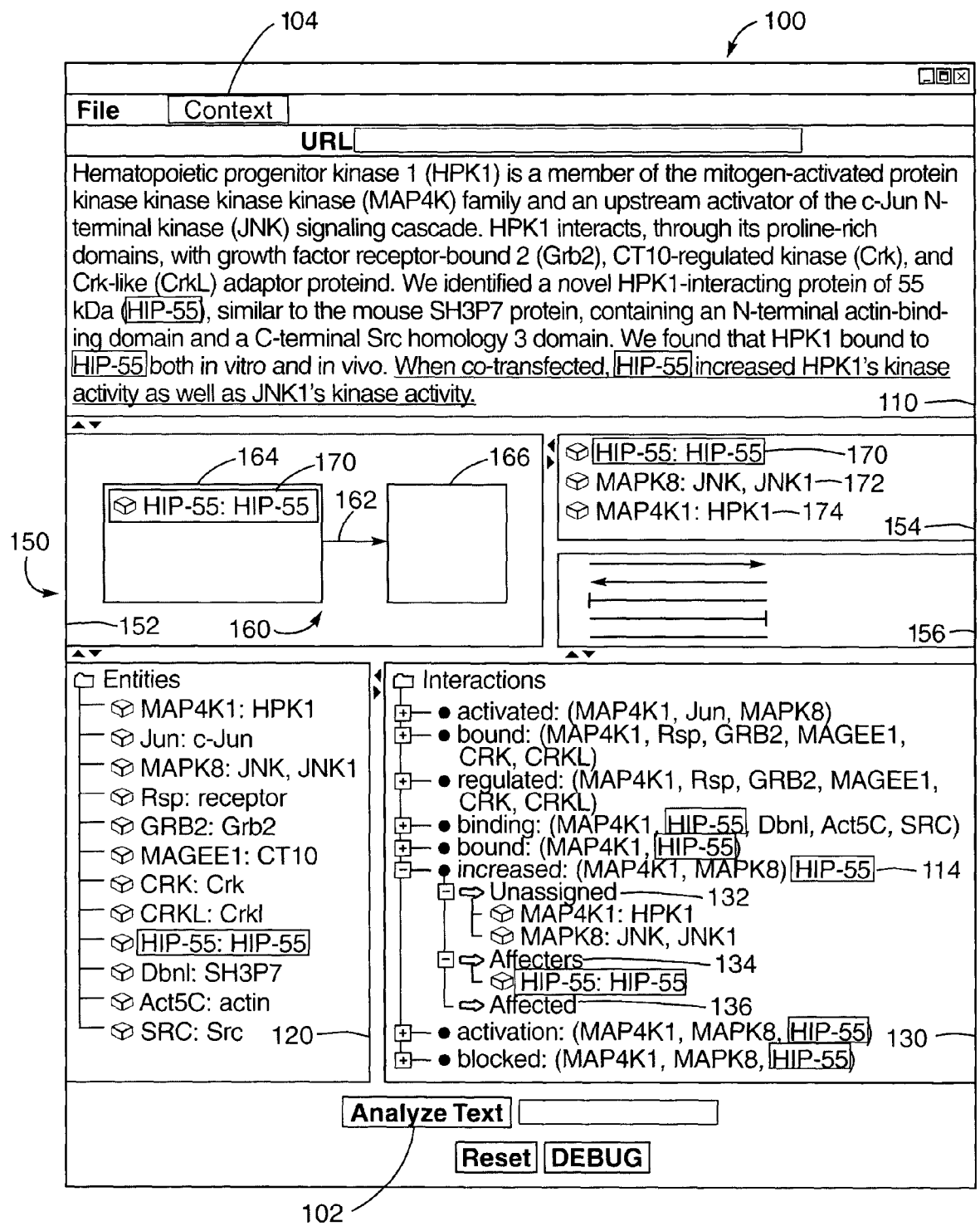
FIG. 3 is an example of a text viewer tool including a diagramming window therewith.

Each entity and interaction in the "Entities" and "Interactions" panels, 120, 130 respectively, also points back to all sections of text 110 that it occurs in, as provided for by the local format linking. For example, FIG. 2 shows an underlined sentence in the "Text" panel 110 with highlighted entities 112 and interactions 114 corresponding to the highlighted interaction 114 in the "Interactions" panel 130. Each interaction in the interaction panel 130 further lists the potential entities involved in the interaction along-with properties of the interaction and entities, context under which the interaction occurs, and any required conditions that have to be met. Each interaction also has slots or blank entry spaces provided where the user can assign entities to the particular roles that they play in that interaction. For example, an entity may be assigned to an "affecter" or "affected" role, depending if the entity is the subject or the object of the verb corresponding to the interaction of interest. This assignment of roles can be used for assigning directionality to the interaction, as it is consistent with current notation where an arrow is drawn to represent an interaction between two entities, to originate from the "affecter" entity and point toward and terminate at the "affected" entity. According to the present invention, in order to make such an assignment, a user can simply select, or click on the "+" icon to the left of the interaction to be worked on, which opens a list of subentries beneath the listed interaction. An example of the results of such a selection by a user is shown in FIG. 3, where the "+" icon adjacent to the "increased" interaction 114 has been selected, which converts it to a "−" icon when the subentries menu opens. The user can then drag entities from the "Unassigned" subentry 132 to the "Affecter" subentry 134 or the "Affected" subentry 136. Entities 112 can also be dragged from the "Entities" list 120 into these subentries. Once entities are dragged into the respective subentries 134,136, the list title defines the relationship between entities (i.e., interaction) in an unambiguous way through this process of disambiguity, since the directionality of the interaction is defined by assignment of entities to the "affecter" and "affected" roles.

For example, completion of the disambiguation process for the entities and interactions highlighted in FIG. 2 would result in subentries under the interaction "increased" 114 listing HIP-55 under the Affecters subentry 134, and listing HPK1 as well as JNK1 under the Affected subentry 136. This gives the user a concise summary of the interaction. Any unassigned entities in the interaction are listed under the Unassigned subentry 132, and may be displayed in parentheses.

Tool 100 also allows the user to define new entities and interactions in these panels. This may be accomplished by pressing the right mouse button, for example, in either panel, which causes a pop-up menu to be presented to the user. Among the available options on the pop-up menu are "New Entity" and "New Interaction". Selection of one of these options causes a new editor window to appear. The new editor window may be used as an interface to create a new entity or interaction and associate the new entity or interaction with section(s) of the text, thereby mimicking the behavior of the automated analysis algorithm of the tools' software.

Optionally, tool 100 may include a diagramming window 150 which a user can drag interactions and entities into to display the interactions and entities diagrammatically. An example of a diagramming tool into which such a list may be dragged is described in co-pending, commonly assigned application Ser. No. 10/155,405, filed May 22, 2002 and titled "Database Model, Tools and Methods for Organizing Information Across External Information Objects". application Ser. No. 10/155,405 is hereby incorporated herein, in its entirety, by reference thereto. Alternatively, the user may drag entities, prior to assigning them as affectors or affected in the Interactions window, directly into the diagramming tool 150. A determination as to whether an entity is an affecter or affected is determined, in this method, by the location that the entity is dragged to in the diagram. Thus, for example, if HIP-55 were dragged from the Entities list 120 to box 164, the results of which are shown at 170 in box 164 (FIG. 3), then an assignment of HIP-55 to the "affecter" role would automatically be made, as shown in the "Affecters" subentry 134. Since all the windows are simultaneous views of the same collection of local format objects, this assignment by the user automatically populates HIP-55 as an affector in the Interactions window 130 and in window 152, for example.

Accordingly, tool 100 provides functionality for the user to assign directionality and causality to interactions among entities. For potentially more powerful, natural and/or intuitive ways to display such information and acquire a user's assignments, the present invention further provides tools and methods for displaying a network of the relationships discussed above. It is generally most intuitive to display and manipulate networked information diagrammatically. For example, diagrams are used as a natural way of representing biochemical reactions or signaling pathways. Hence, FIG. 3 shows an example of the present invention provided by tool 100, which includes an optional graphical pane 150, as alluded to above. Pane 150 is adapted to contain a diagrammatic representation for one or more interactions. This feature provides the user with an alternate, intuitive mechanism to disambiguate and assign directionality and causality to extracted knowledge, resulting in a richer and more correct encoding of extracted biological knowledge.

The graphical pane 150 may be a single pane in which a simple graphical representation of an interaction is populated, or, alternatively may be divided into two or more areas, as shown in FIG. 3. When a single pane is used, entities may be dragged directly into the boxes 164 and 166 of an empty diagram to populate it with those entities so as to disambiguate the directionality of the interaction that the entities are involved in. In a multi-pane configuration, as shown, the left side pane may be a canvas area 152 which may be used for representing unassigned interactions and entities (e.g., see the boxes 164, 166 and arrow 162) and making assignments to them. On the right side palette areas 154, 156 may be provided into which entities and interactions may be populated (such as by dragging and dropping, for example) 154. Further optionally, pane 156 may contain "building blocks" that can be used to construct custom graphical representations of biological interactions.

The initial setup for using tool 100 with the optional graphics functionality is the same as that described above for use of tool 100 without the graphics window. As a practical example, a user, such as a scientific researcher, may perform a scientific literature search to look for particular entities and/or interactions that have been identified over the course of some experimentation done. A scientific literature search may be performed, for example, using the tools and methods described in co-pending, commonly owned application Ser. No. 10/033,823, filed Dec. 19, 2001 and titled "Domain-Specific Knowledge-Based MetaSearch System and Methods of Using". application Ser. No. 10/033,823 is hereby incorporated herein, in its entirety, by reference thereto. The search results delivered may include a large number of textual documents that have been determined to be relevant to the search, which may define entities and/or interactions of interest.

Using viewer tool 100, an article, abstract thereof, or other selected portion thereof can be imported into window 110. Based upon user defined preferences, also known as the user context, (e.g., listing entities and interactions of interest, which is generally much more extensive than the search string that was used to perform the literature search), viewer 100, upon selecting or clicking on "Analyze Text" 102 automatically identifies the entities and interactions defined in the user defined preferences and highlights the same as shown in window 110. At the same time, the entities which are identified are populated in Entities window 120 and the interactions that are identified are populated in Interactions window 130.

Thus, when a textual document, such as a publication or an extract from a publication is inputted into the text viewer window 110 of tool 100, in a manner as described above, and the user selects the "Analyze Text" button 102, tool 100 responds by using user context and local format tools and methods to identify the nouns and verbs contained within the textual material, extract them, and list them in the entities window 120 and interactions window 130, as shown. Each item in the list structure for interactions 130 is a visual representation of the underlying local format, restricted grammar representation of that interaction. Automated analysis using lexicons for entities and interactions may be used to identify the interesting nouns and verbs (e.g., those matching or related to an item in a lexicon) in every sentence of the text. Simple rules may be applied to break down the text into sentences. The identified nouns are represented in the "Entities" list 120, while the verbs are represented in the "Interactions" list 130, as noted above.

Each entity and interaction in the "Entities" and "Interactions" panels, 120, 130 respectively, also points back to the part of text 110 it occurs in, as provided for by the local format linking, the same as was described above with regard to the example shown in FIG. 2. Each interaction in the interaction panel 130 further lists the potential entities involved in the interaction, along with properties of the interaction and entities, context under which the interaction occurs, and any required conditions that have to be met.

The user may next select one of the interactions from the interactions pane 130, such as by clicking on it with the mouse, for example, or through use of keyboard strokes. The canvas 152 and palette 154 may be, in response to the selection, automatically populated according to the contents of the highlighted interaction, as shown in FIG. 3. Canvas 152 may be populated with a diagram or graphical rendering 160 that is predesigned for a simple promotion interaction (i.e., describing an "increased" interaction), for example. The arrowed line 162 (which may be color-coded, e.g., red) running between the rectangles 164 and 166 indicates the promotion interaction and its direction, i.e., that entity 164 increases entity 166. The rectangles 166 (which may also be color coded, e.g., lavender) are "bounding boxes" for the affecter (box 164) and affected (box 166) entities, respectively. The entities involved in the interaction are shown in the palette 154. Icons for additional interactions and their directionality may be provided, as shown in palette 156, for example.

Figure 4A:
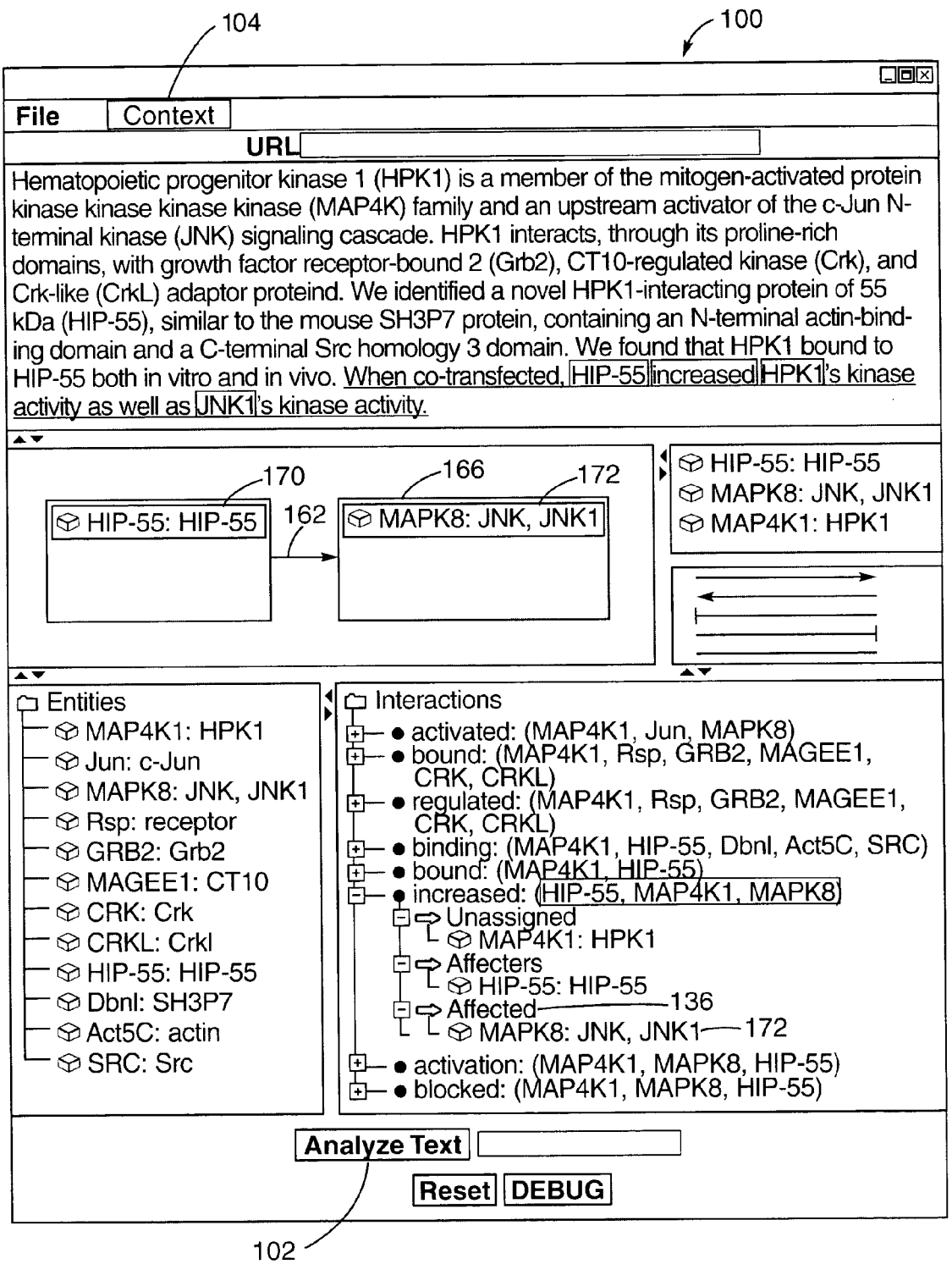
FIGS. 4A–4B show the tool of FIG. 2 after various stages of populating a graphical representation in the canvas of the diagramming window.
Figure 4B:
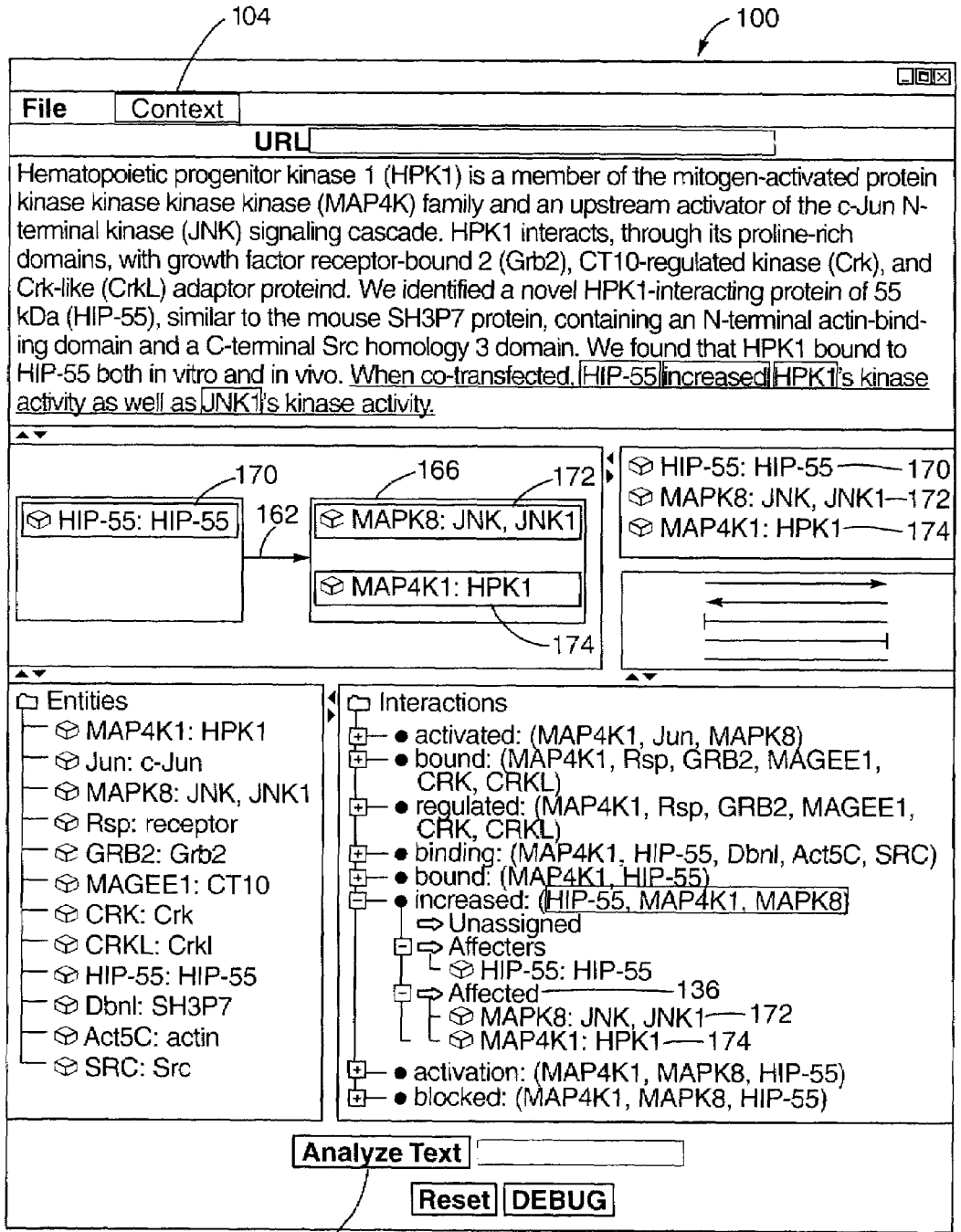

The user next begins to populate diagram 160 with entities from palette 154 by repetitively dragging entities from the palette area 154 over to one of the "bounding boxes" in the graphical pane. In this example, entity 170 (i.e., HIP-55:HIP-55) is dragged from palette area 154 to the affecter box 164 and dropped. The result of this operation is shown in FIG. 3. The dragged/dropped entity 170 is then assigned by the system as an affecter 134 in the interaction "increased" 114 as also shown in FIG. 3. The user in this example next selects additional entities 172, 174 from palette 154 area and drags them into the affected bounding box 166 and drops them there. Entities 172 and 174 are consequently automatically assigned as affecteds 136 in the interaction "increased" 114 as shown sequentially in FIGS. 4A and 4B. Additionally or alternatively, entities and/or interactions may be dragged from the Entities panel 120 and/or Interactions panel 130 into the slots in the canvas area 152.

As a result of these actions, the user has graphically disambiguated the interaction and has automatically established this disambiguous relationship textually, resulting in both textual and graphical representations of the interaction which are directionally unambiguous. It is noted that that present invention may also be used to disambiguate according to the techniques described with reference to FIG. 2, to establish directionality in the local format text annotation in pane 130. The user may then select the "increased" interaction, for example, to automatically construct a filled in diagram, which would appear the same as the completed diagram 160 in FIG. 4B. By this functionality, the present invention serves as a tool for rapid and unambiguous construction of biological diagrams.

After disambiguating all of the knowledge extracted from a textual document in any of the manners described above, viewer 100 may next construct or draw a biological diagram representative of all of the disambiguated interactions that the document contains. Such construction may be done in an additional viewer pane, like the type shown in FIG. 5, for example, or sent to a diagram viewer 200. Of course, it is not necessary to complete disambiguation of all entities and interactions with regard to a textual document being examined, although this is the normal course that a user would follow. Diagram construction may be performed at any stage along the disambiguation process, at which time a diagram is constructed based upon entities and interactions which have been disambiguated thus far.

For example, a user may select an abstract, textual document, or a portion thereof and import it into textual viewer 100 as described above. By engaging the "Analyze Text" 102 feature, the present invention identifies all entities and interactions in the textual document (or portion of a document) based on a predefined user context. The user context includes, for example, a list of keywords. Currently the present system is adapted to read XML or Excel files, although it would be apparent to one of ordinary skill in the art to extend the capability to other known formats. Each entry in the user context generally includes an identifier as to whether the entry is a noun or a verb; the name of the entry (i.e., which contributes to the lexicon for searching); the type that the entry is (e.g., cell, process, disease, or the like for nouns; bind, promote, inhibit, or the like for verbs); and aliases for the name of the entry, which are also added to the lexicon. However, the user context may still function with only a subset of such information, although less effectively (e.g., aliases could be omitted for some entries). Of course further descriptive information categories could be included for characterizing one or more entries in the user context, as would be readily apparent to one of ordinary skill in the art.

Additionally or alternatively, an existing diagram (whether manually drawn or a pre-existing machine format diagram) or portion thereof may be used to define a user context. Using a diagram viewer, such as described application Ser. No. 10/641,492 for example, the diagram or portion thereof is converted to the local format. Once the conversion has been completed, the local format representation of the nouns and verbs represented diagrammatically are populated into the user context upon which a textual analysis may be based. More generally, any information which has been converted to the local format (e.g., experimental data, or other data) may be used to populate the user context.

If the user highlight or selects one or more entities and/or interactions from the entities and/or interactions lists 120, 130, the tool automatically highlights those same entities and/or interactions in the text in window 110, via the linking provided by the local format data objects underlying the system. Because it is difficult to determine directionality of relationships/interactions identified solely through the use of natural language programming techniques, the user is involved, in the next step, in the process of disambiguating the relationships, as noted above. Once interactions have been disambiguated, the user can select all or a portion of the disambiguated relationships listed, and a diagram view of the relationships is generated by linking like entities, using the local format architecture, for example. It should also be noted here, that a diagrammatic view can be generated prior to disambiguating all information and the disambiguation process can be performed on the diagram view, using techniques described above, as well as in application Ser. No. 10/641,492.

The user may then wish to import another abstract, textual document, or a portion thereof, and iterate the process described above. After disambiguation of interactions/relationships in this next document, relationships and entities which are common to those identified in previous textual documents can be identified, either automatically or manually, and this information is joined to the previously created biological diagram.

Disambiguation can be performed with respect to each document, as the documents may not always agree as to the mechanism of an interaction. Where there is disagreement, upon generating a graphical diagram, the diagram will indicate such discord. As a simple example, if a first document indicates that entity A increases entity B, while a second article indicates that entity A decreases entity B, then the graphical representation may show a block for A, a block for B, and two lines extending between A and B. The lines may be differentiated by color coding (e.g., one green and one red) and/or by different arrowheads pointing towards B, e.g., one with an arrow-shaped arrowhead (i.e., - →) for a promotion and one with a blocked arrowhead (i.e., - - - |) to indicate an inhibition, for example. Other visual differentiators may be used in addition to, or alternatively to those described.

When more than one document contains an interaction that is displayed in a graphical diagram, annotations are made to that portion of the diagram which link that interaction to each of the documents where it occurs. Thus, not only is that interaction linked directly, such a by a hyperlink, but other annotations may be included to suit the user's needs, such as described for example in application Ser. Nos. 10/155,304, 10/155,616 and 09/863,115, all of which are incorporated herein, in their entireties, by reference thereto.

Figure 5:
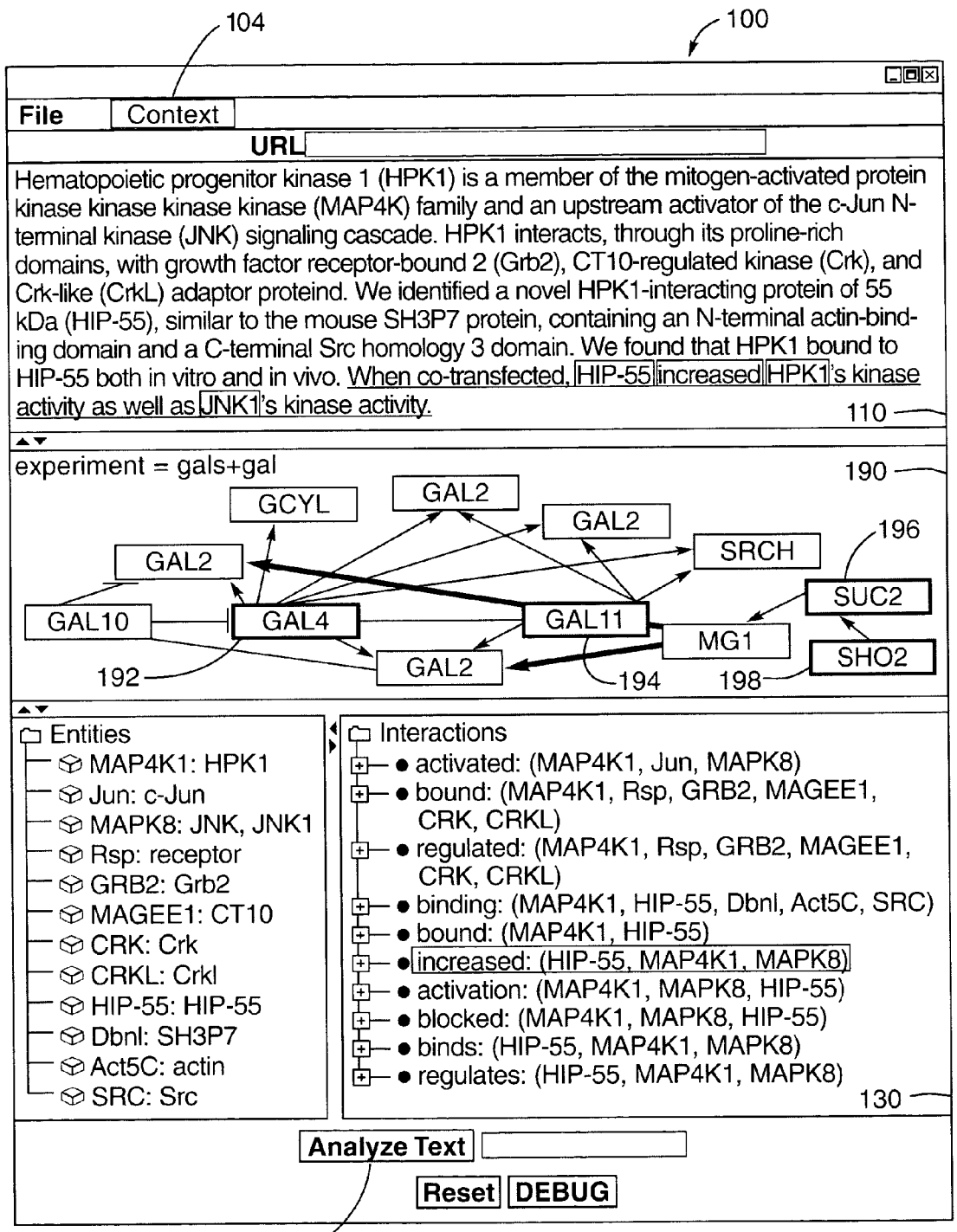
FIG. 5 shows a tool according to the present invention which may be used to build networks of interactions by composing entities, interactions, and graphical renderings. A user can associate the resultant network with experimental data values, performing an informal verification of the putative network against actual data.

Thus, the present invention further provides the ability to build networks of interactions by composing entities, interactions, and diagrams. Using this feature, the user selects a subset of interactions in the "Interactions" list 130 and drags them into a separate network viewer window 190, as shown in FIG. 5. Alternatively, the selected interactions may be automatically populated into viewer window 190 upon their selection. The system may merge interactions with common entities, forming a graph structure.

The graph structure can be built upon by analyzing an additional textual document and processing it as described above with regard to the first textual document. Upon identifying and disambiguating the interactions in the second textual document, these interactions can then be joined in the graphical composition. This type of building can be done repeatedly with as many textual documents as desired.

Figure 6A:
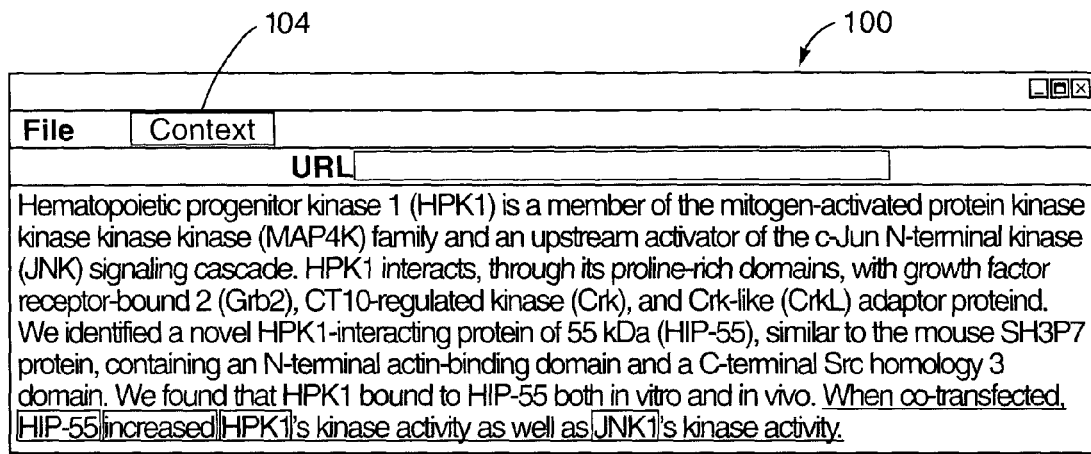
FIGS. 6A–6B show a tool providing the ability to compare extracted knowledge against an existing biological network.
Figure 6A:
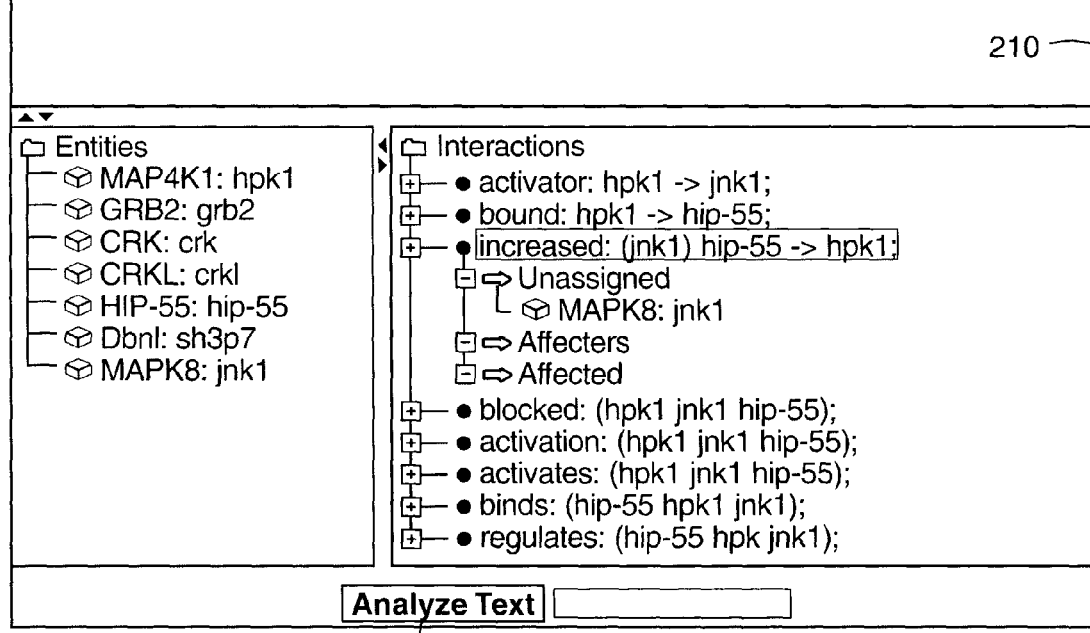
Figure 6B:
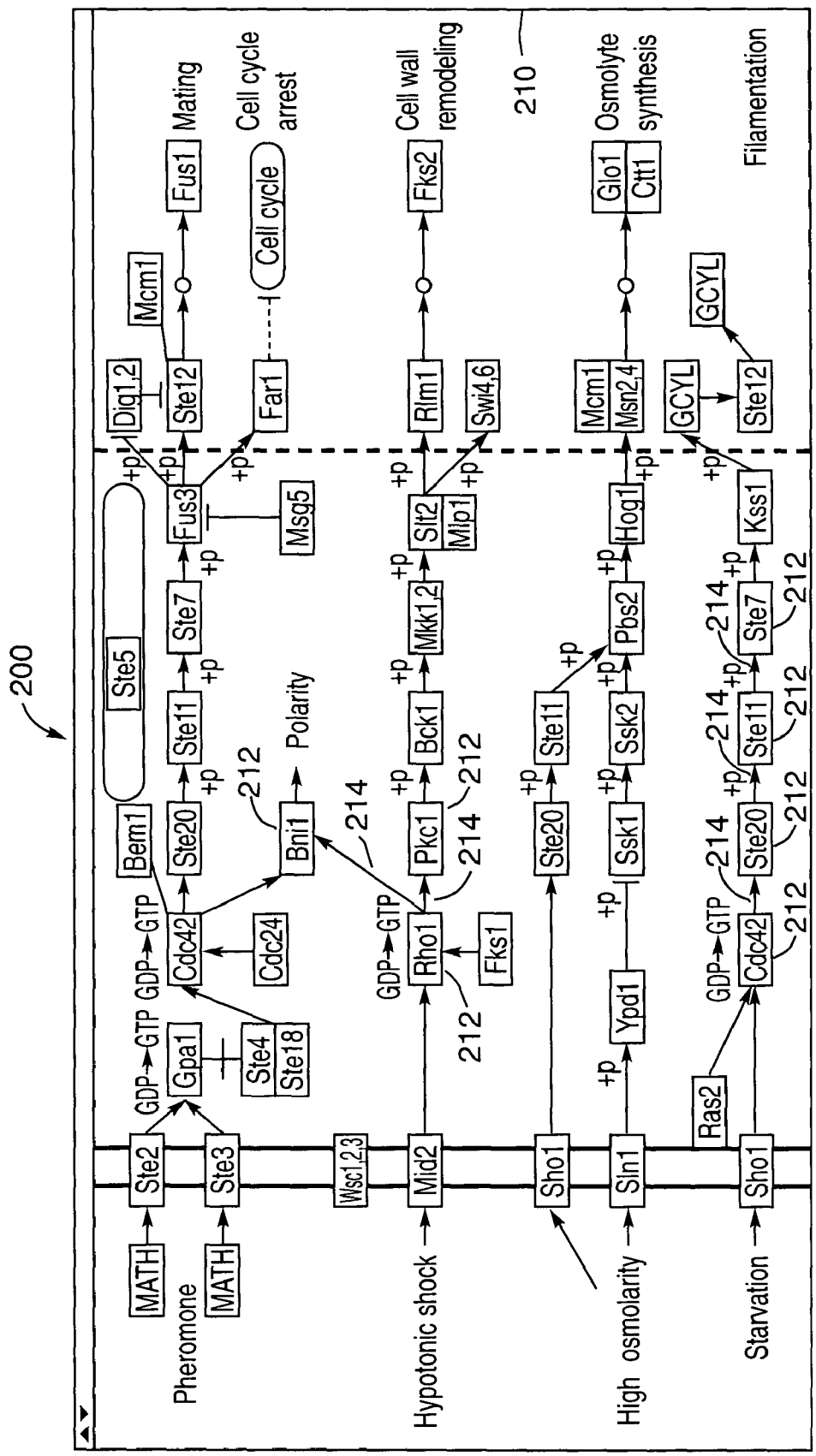

The present invention further provides the ability to compare extracted knowledge against an existing biological network. The user can load an existing network diagram into the system or select a subset of an existing network via search. The system overlays the extracted interactions and their entities upon the imported diagram, such as by color-coding those nodes and arcs in the imported diagram that correspond to extracted entities and interactions, for example. An example of this functionality, using a Mapkinase signaling pathway diagram 210 imported from the KEGG web site (http://www.kegg.org), is schematically shown in FIGS. 6A–6B. The color-coded nodes 212 and links 214 indicate the overlays of the extracted interactions and their entities. A further aspect of this overlay technique uses an automated approach to search for existing networks that contain a user-specified set of interactions. The networks found to include the specified set of interactions are then provided to the user for selection among this set to overlay the extracted interactions and entities.

The present invention may also be deployed in batch mode, in conjunction with a biological textual search tool, such as that described in copending, commonly owned application Ser. No. 10/033,823, for example. In this mode, the researcher may perform a scientific literature search, as described above, but instead of simply analyzing one document at a time, tool 100 may be tasked to analyze all documents (or some subset thereof) returned from the search, in batch mode. The result is a combined list of entities and interactions extracted from all of the documents processed. This may simplify the user's ability to compare and contrast among the textual documents during the process of disambiguation which can be performed next. Also, any generation of larger scale diagrams from the disambiguated entities and interactions may be facilitated, by the user being able to view all entities and interactions together.

Upon selecting an interaction in batch mode, text viewer window 110 may be adapted to identify each textual document that the interaction occurs in. For an example of batch processing, a literature search may be performed using a domain-specific, knowledge-based metasearch system, such as that described in application Ser. No. 10/033,823, which allows the user to specify particular scientific databases to search. The search may return a sizeable number of relevant documents. For example, assuming fifty to one hundred relevant documents are returned in the search results, then the system described in application Ser. No. 10/033,823 may be used to extract relevant text from these documents in batch mode, e.g., to text mine and identify abstracts and portions of text containing the search words.

Once such portions and abstracts have been identified and imported into tool 100, the user may select "Analyze Text" and identify all nouns and interactions in the entire batch of identified portions and abstracts, based on a predefined user context. By highlighting any identified noun or interaction, an annotation link shows, in the text viewer, where in text the highlighted entity(ies) and/or interaction(s) is/are located. It is difficult to determine directionality of relationships/interactions using natural language programming alone. Therefore, the user is involved, in the next step, in the process of disambiguating the relationships, just as described above with regard to non-batch processing modes. Once all interactions have been disambiguated, the user can select all or a portion of the relationships listed, and a diagram view of the relationships is generated by linking like entities.

Disambiguation can be performed with respect to each document, as well as across a corpus of documents, by processing in batch mode. However, all documents may not always agree as to the mechanism of an interaction. Where there is disagreement, upon generating a graphical diagram, the diagram will indicate such discord. As a simple example, if a first document indicates that entity A increases entity B, while a second article indicates that entity A decreases entity B, then the graphical representation may show a block for A, a block for B, and two lines extending between A and B. The lines may be differentiated by color coding (e.g., one green and one red) and/or by different arrowheads (e.g., an arrow-shaped arrowhead indicating promotion, and a blocked arrowhead indicating inhibition) each pointing toward block B. Other visual differentiators may be used in addition to, or alternatively to those described.

When more than one document contains an interaction that is displayed in a graphical diagram, annotations are made to that portion of the diagram which link that interaction to each of the documents where it occurs. Thus, not only is that interaction linked directly, such a by a hyperlink, but other annotations may be included to suit the user's needs.

The present invention may also be used for alias management, that is to track and equate various names that are used for the same entity or interaction, for example, as described above. This function may be used to supplement the Biological Information Naming System described in co-pending, commonly owned application Ser. No. 10/154, 529, filed May 22, 2002, and titled "Biotechnology Information Naming System", which is incorporated herein, in its entirety, by reference thereto. For example, referring back to FIG. 2, tool 100 identified two entities 118 (JNK) and 119 (JNK1) among all of the entities identified. Employing the Biotechnology Information Naming System to look up each entity, tool 100 then determines that JNK and JNK1 refer to the same entity (the formal name of which is MAPK8). Upon making this determination, both JNK and JNK1 are automatically listed on the same entity line in Entities window 120, as shown in FIG. 2. Additionally, tool 100 manages these aliases by highlighting both in the text viewer 110 when the user is interested in identifying interactions involving either JNK or JNK1. This provides a powerful visual reminder to the user of the equivalency among the aliases.

Figure 7:
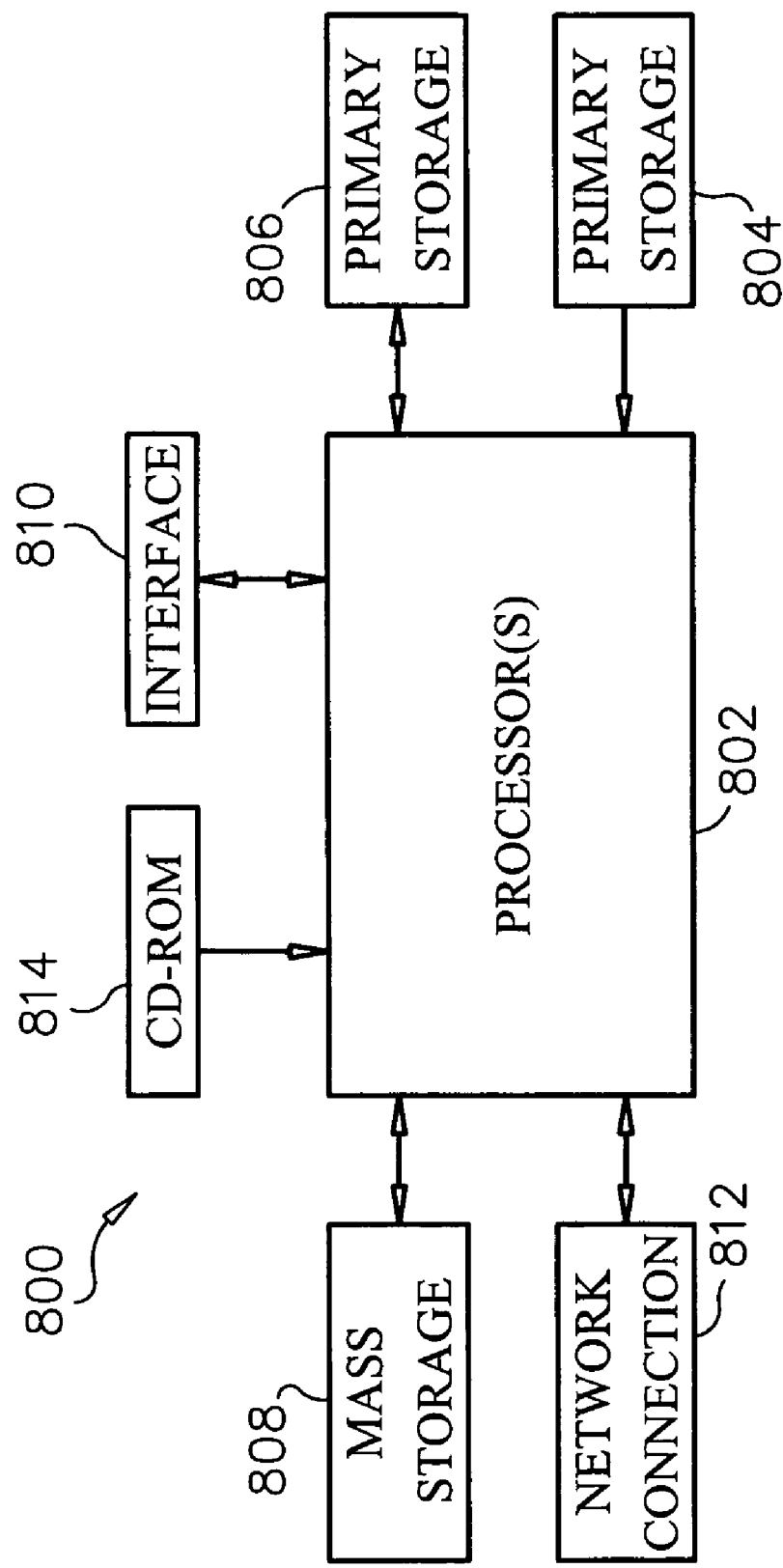
FIG. 7 is a block diagram illustrating an example of a generic computer system which may be used in implementing the present invention.

FIG. 7 illustrates a typical computer system in accordance with an embodiment of the present invention. The computer system 800 includes any number of processors 802 (also referred to as central processing units, or CPUs) that are coupled to storage devices including primary storage 806 (typically a random access memory, or RAM), primary storage 804 (typically a read only memory, or ROM). As is well known in the art, primary storage 804 acts to transfer data and instructions uni-directionally to the CPU and primary storage 806 is used typically to transfer data and instructions in a bi-directional manner Both of these primary storage devices may include any suitable computer-readable media such as those described above. A mass storage device 808 is also coupled bi-directionally to CPU 802 and provides additional data storage capacity and may include any of the computer-readable media described above. Mass storage device 808 may be used to store programs, data and the like and is typically a secondary storage medium such as a hard disk that is slower than primary storage. It will be appreciated that the information retained within the mass storage device 808, may, in appropriate cases, be incorporated in standard fashion as part of primary storage 806 as virtual memory. A specific mass storage device such as a CD-ROM 814 may also pass data uni-directionally to the CPU.

CPU 802 is also coupled to an interface 810 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 802 optionally may be coupled to a computer or telecommunications network using a network connection as shown generally at 812. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for text mining and conversion to the local format may be stored on mass storage device 808 or 814 and executed on CPU 808 in conjunction with primary memory 806.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular model, tool, process, process step or steps, to the objective, spirit and scope of the present invention. All such modifications are intended to be within the scope of the claims appended hereto.

The invention claimed is:

1. A tool providing interactive capabilities for user involvement in extracting and disambiguating biological information in text, said tool comprising:
   a text viewer into which at least a portion of a textual document is importable and viewable, said text viewer including a display on which said at least a portion of the text document is viewable;
   means for text mining the at least a portion of a textual document having been imported into the text viewer to extract nouns and verbs therefrom;
   a list-based text editor that lists nouns and verbs extracted by said means for text mining as entities and interactions;
   means for assigning directionality to the listed interactions;
   means for converting the extracted nouns and verbs into a local format representation as the entities and interactions; and
   means for generating, displaying and interactively manipulating a biological diagram, based upon the entities and interactions represented in said local format.

2. The tool of claim 1, wherein each said entity and interaction listed points back to a location of the portion of the textual document where it was identified.

3. The tool of claim 1, wherein said means for assigning includes slots associated with each said interaction, to which a user can identify one or more of said entities involved in the interaction, and assign roles of each said entity played in the interaction.

4. The tool of claim 3, wherein said roles comprise affecters, affected and unassigned.

5. The tool of claim 4, wherein said roles further comprise mediator and unknown.

6. The tool of claim 1, further comprising a user context, wherein said means for text mining text mines based upon contents of said user context.

7. The tool of claim 6, wherein said user context comprises at least one entity or interaction.

8. The tool of claim 6, further comprising means for managing said user context, wherein said means for managing permits editing of an existing user context, as well as creation of a new user context.

9. The tool of claim 8, wherein said means for managing allows selection of specific entities and interactions to be added to said user context.

10. The tool of claim 8, wherein said means for managing allows direct inputting of entities and interactions into said user context.

11. The tool of claim 8, wherein said means for managing facilitates selection of local format representations of entities and interactions, and entering said local format representations into said user context.

12. The tool of claim 1, further comprising a user context, wherein said means for text mining text mines based upon contents of said user context; and
   means for managing said user context, wherein said means for managing permits editing of an existing user context, as well as creation of a new user context, and wherein said means for managing facilitates selection of local format representations of entities and interactions generated from said manipulation of a biological diagram.

13. The tool of claim 6, further comprising means for managing aliases, wherein said means for managing aliases equates multiple names for the same entity, enabling said tool to identify each said entity by multiple names as they occur in the textual documents.

14. The tool of claim 13, further comprising means for resolving errors in alias management.

15. A tool providing interactive capabilities for user involvement in extracting and disambiguating biological information in text, said tool comprising:
   a text viewer into which at least a portion of a textual document is importable and viewable, said text viewer including a display on which said at least a portion of the text document is viewable;
   means for text mining the at least a portion of a textual document having been imported into the text viewer to extract nouns and verbs therefrom;
   a list-based text editor that lists nouns and verbs extracted by said means for text mining as entities and interactions;
   a canvas area for diagrammatically representing said entities and interactions;
   means for populating diagrammatic renderings on said canvas with one or more of said entities and interactions identified by said means for text mining;
   means for representing said entities and interactions in a local format; and
   means for generating, displaying and interactively manipulating a biological diagram, based upon the entities and interactions represented in said local format.

16. The tool of claim 15, wherein said means for populating includes means for assigning directionality of interactions.

17. The tool of claim 15, further comprising a palette for containing entities and interactions selected by a user from lists displayed by said list-based text editor, wherein said entities and interactions in said palette are draggable to said canvas to populate a diagrammatic rendering.

18. The tool of claim 15, wherein, upon populating a diagrammatic rendering, assignments of roles played by entities populating said diagrammatic rendering are automatically assigned in a list displayed by said list-based text editor.

19. The tool of claim 15, further comprising means for adding elements to a diagrammatic rendering on said canvas by freehand sketching by the user.

20. The tool of claim 19, wherein each said entity and interaction displayed on said canvas and listed in said list-based text editor points back to a location of the portion of the textual document where it was identified.

21. The tool of claim 15, wherein said diagrammatic renderings are populated by selecting at least one entity or interaction from said list-based text editor and dragging to a desired location in a diagrammatic rendering displayed on the canvas.

22. The tool of claim 15, wherein said diagrammatic renderings are populated by selecting at least one entity or interaction from said text in said text viewer and dragging to a desired location in a diagrammatic rendering displayed on the canvas.

23. A tool for building biological networks of interactions from text, said tool comprising:
   a text viewer into which at least a portion of a textual document is importable and viewable, said text viewer including a display on which said at least a portion of the text document is viewable;
   means for text mining the at least a portion of a textual document having been imported into the text viewer to extract nouns and verbs therefrom;
   a list-based text editor that lists nouns and verbs extracted by said means for text mining as entities and interactions;
   means for assigning directionality to the listed interactions; and
   means for selecting interactions and associated entities in the list-based editor, merging common entities and displaying a resulting biological network of the interactions in a window of said text view or in a separate network viewer; and
   means for interactively manipulating the biological network.

24. The tool of claim 23, further comprising means for representing said entities and interactions in a local format.

25. A tool for comparing extracted biological knowledge extracted from text, against an existing biological diagram, said tool comprising:
   a text viewer into which at least a portion of a textual document is importable and viewable, said text viewer including a display on which said at least a portion of the text document is viewable;
   means for text mining the at least a portion of a textual document having been imported into the text viewer to extract nouns and verbs therefrom;
   a list-based text editor that lists nouns and verbs extracted by said means for text mining as entities and interactions;
   a diagram viewer and means for importing at least a portion of an existing biological diagram into said diagram viewer;
   means for overlaying the identified entities and interactions on said at least a portion of an existing biological diagram that is displayed in said diagram viewer;
   means for visually distinguishing the overlaid entities and interactions from a remainder of the displayed biological diagram; and
   means for interactively manipulating the biological diagram.

26. The tool of claim 25, further comprising means for representing said entities and interactions in a local format.

27. The tool of claim 25, wherein each said entity and interaction overlaid points back to a location of the portion of the textual document where it was identified.

28. The tool of claim 25, further comprising means for assigning directionality to the listed interactions; means for selecting interactions and associated entities in the list-based editor and populating diagrammatic renderings representing said selected interactions and associated entities, wherein said populated diagrammatic renderings are overlaid on the at least a portion of an existing biological diagram displayed in said diagram viewer.

29. The tool of claim 28, further comprising means for converting the at least a portion of an existing biological diagram to a local format, and based on values contained in the local format, comparing said diagrammatic renderings with corresponding parts of the existing biological diagram.

30. The tool of claim 25, further comprising means for automatically searching databases of existing biological diagrams that contain a user-specified set of interactions and returning those existing biological diagrams that contain the user-specified set of interactions to the user for display in said diagram viewer for use in overlaying and comparing the identified entities and interactions therewith.

31. A method of providing interactive capabilities for user involvement in extracting and disambiguating biological information in text, said method comprising the steps of:
   importing at least a portion of a textual document into a text viewer, said text viewer including a display on which said at least a portion of the text document is viewable;
   text mining the at least a portion of a textual document to extract nouns and verbs therefrom and identify the nouns and verbs as biological entities and interactions;
   listing the identified entities and interactions in a list-based text editor;
   assigning directionality to the listed interactions by associating listed entities as affecters or affecteds with respect to the interactions;
   converting at least a portion of a biological diagram to local format objects representing entities and interactions displayed in the biological diagram;
   inputting at least a portion of said local format objects into a user context; and,
   performing said text mining based upon the contents of the user context.

32. The method of claim 31, further comprising representing said entities and interactions in a local format.

33. The method of claim 31, further comprising providing a user context, wherein said user context comprises data upon which said text mining is based.

34. The method of claim 33, further comprising managing said user context to edit the contents thereof or to create a new user context.

35. The method of claim 34, wherein said managing comprises selecting at least one entity or interaction and adding the selection to the user context.

36. The method of claim 34, wherein said managing comprises directly inputting at least one entity or interaction to the user context by a user, or editing existing data, by the user, in the user context.

37. The method of claim 34, wherein said managing comprises selecting at least one local format representation of an entity or interaction, and entering said at least one local format representation into the user context.

38. The method of claim 31, further comprising managing aliases of entities and interactions, to equate multiple names for the same entity or interaction, so that said text mining, listing and assigning directionality steps are carried out with respect to aliases of entities and interactions contained in the user context, as well as the actual names contained in the user context.

39. The method of claim 38, further comprising resolving errors in alias management.

40. The method of claim 39, wherein said error resolution is carried out interactively by a user.

41. The method of claim 32, further comprising at least one of the steps selected from the group consisting of:
   generating a biological diagram based on said entities and interactions represented in said local format;
   displaying a biological diagram based on said entities and interactions represented in said local format; and
   interactively manipulating a biological diagram based on said entities and interactions represented in said local format.

42. The method of claim 31, further comprising linking each listed entity and interaction with a location in the textual document from which each listed entity and interaction was identified, respectively, using a local format.

43. The method of claim 31, further comprising the steps of:
   providing a canvas area for diagrammatically representing said entities and interactions;
   populating at least one diagrammatic rendering on the canvas with one or more of said entities and interactions identified by said means for text mining.

44. The method of claim 43, wherein upon said populating at least one diagrammatic rendering, assignments of roles played by said entities populating said at least one diagrammatic rendering are automatically assigned in a list displayed by said list-based text editor.

45. The method of claim 43, further comprising adding elements to a diagrammatic rendering on said canvas by freehand sketching by a user.

46. The method of claim 43, wherein said diagrammatic renderings are populated by selecting at least one entity or interaction from said list-based text editor and dragging to a desired location in a diagrammatic rendering displayed on the canvas.

47. The method of claim 43, wherein said diagrammatic renderings are populated by selecting at least one entity or interaction from said text in said text viewer and dragging to a desired location in a diagrammatic rendering displayed on the canvas.

48. The method of claim 31, further comprising:
   performing a text search to identify a plurality of textual documents;
   importing all or a subset of the plurality of documents into the text viewer; and
   analyzing the textual documents in batch mode to identify interactions and entities to be listed in the list-based editor.

49. The method of claim 31, further comprising:
   identifying aliases of at least one entity or interaction listed; and
   performing operations on all aliases of the at least one entity or interaction simultaneously with performance of those operations on the at least one entity or interaction.

50. A method comprising forwarding a result obtained from the method of claim 31 to a remote location, wherein said result comprises at least one of a list created by said listing the identified entities and interactions in a list-based text editor, and a listed interaction having had directionality assigned thereto by said step of assigning directionality.

51. A method comprising transmitting data representing a result obtained from the method of claim 31 to a remote location, wherein said result comprises at least one of a list created by said listing the identified entities and interactions in a list-based text editor, and a listed interaction having had directionality assigned thereto by said step of assigning directionality.

52. A method comprising receiving a result obtained from a method of claim 31 from a remote location, wherein said result comprises at least one of a list created by said listing the identified entities and interactions in a list-based text editor, and a listed interaction having had directionality assigned thereto by said step of assigning directionality.

53. A method of providing interactive capabilities for user involvement in extracting and disambiguating biological information in text to be used in generating a biological diagram, said method comprising the steps of:
   importing at least a portion of a textual document into a text viewer, said text viewer including a display on which said at least a portion of the text document is viewable;
   text mining the at least a portion of a textual document to extract nouns and verbs therefrom and identify the extracted nouns and verbs as biological entities and interactions;
   listing the identified entities and interactions in a list-based text editor;
   representing the identified entities and interactions in a local format;
   providing a canvas area for diagrammatically representing entities and interactions having been identified by said text mining;
   populating a diagrammatic rendering on the canvas with one or more of said entities and interactions identified by said means for text mining, including indicating directionality of at least one interaction represented by the diagrammatic rendering; wherein, upon populating the diagrammatic rendering, assignments of roles played by entities populating said diagrammatic rendering are automatically assigned in a list displayed by said list-based text editor; and
   further performing at least one of the steps selected from the group consisting of:
   generating a biological diagram based on said entities and interactions represented in said local format;
   displaying a biological diagram based on said entities and interactions represented in said local format; and
   interactively manipulating a biological diagram based on said entities and interactions represented in said local format.

54. The method of claim 53, wherein each said entity and interaction displayed on said canvas and listed in said list-based text editor is automatically linked with a location of each portion of the textual document where it was identified, using a local format.

55. A method for building biological networks of interactions from text, said method comprising the steps of:
   importing at least a portion of a textual document into a text viewer; said text viewer including a display on which said at least a portion of the text document is viewable;
   text mining the at least a portion of a textual document having been imported into the text viewer to extract nouns and verbs therefrom;
   listing the extracted nouns and verbs as entities and interactions;
   assigning directionality to the listed interactions;
   selecting interactions and associated entities and displaying a resulting network of the interactions and entities;
   representing said entities and interactions in a local format;
   converting the at least a portion of an existing biological diagram to a local format; and
   based on values contained in the local format describing the existing biological diagram, comparing the selected entities and interactions with corresponding parts of the existing biological diagram.

56. The method of claim 55, wherein said selecting and displaying include merging common entities to form a network of interactions and entities.

57. The method of claim 55, further comprising the steps of:
   automatically searching databases of existing biological diagrams that contain a user-specified set of interactions; and
   returning existing biological diagrams that contain the user-specified set of interactions to the user for use in said overlaying the identified entities and interactions on at least a portion of an existing biological diagram.

58. A computer readable medium embodying one or more sequences of instructions for user involvement in extracting and disambiguating biological information in text to be used in generating a biological diagram, wherein execution of one or more sequences of instructions by one or more processors results in performing the steps of:
   importing at least a portion of a textual document into a text viewer; said text viewer including a display on which said at least a portion of the text document is viewable;
   text mining the at least a portion of a textual document to extract nouns and verbs therefrom and identify the extracted nouns and verbs as biological entities and interactions;
   listing the identified entities and interactions in a list-based text editor;
   assigning directionality to the listed interactions by associating listed entities as affecters or affecteds with respect to the interactions;
   converting the extracted nouns and verbs into a local format representation as the entities and interactions; and
   generating, displaying and interactively manipulating a biological diagram, based upon the entities and interactions represented in said local format.

59. The computer readable medium of claim 58, wherein execution of one or more sequences of instructions by one or more processors causes the one or more processors to perform the additional step of linking each listed entity and interaction with a location in the textual document from which each listed entity and interaction was identified, respectively, using the local format.

60. The computer readable medium of claim 58, wherein execution of one or more sequences of instructions by one or more processors causes the one or more processors to perform the additional steps of:
   providing a canvas area for diagrammatically representing said identified entities and interactions; and
   populating at least one of the diagrammatic renderings on the canvas with one or more of said entities and interactions identified by said means for text mining.

61. The computer readable medium of claim 60, wherein execution of one or more sequences of instructions by one or more processors causes the one or more processors to perform the additional steps of adding elements to a diagrammatic rendering on the canvas or creating a diagrammatic rendering on the canvas by freehand sketching.

62. The computer readable medium of claim 60, wherein execution of one or more sequences of instructions by one or more processors causes the one or more processors to perform the step of populating said diagrammatic renderings, upon selection of at least one entity or interaction from said list-based text editor and dragging to a desired location in a diagrammatic rendering displayed on the canvas.

63. The computer readable medium of claim 60, wherein execution of one or more sequences of instructions by one or more processors causes the one or more processors to perform the step of populating said diagrammatic renderings, upon selection of at least one entity or interaction from said text in said text viewer and dragging to a desired location in a diagrammatic rendering displayed on the canvas.

64. The computer readable medium of claim 58, wherein execution of one or more sequences of instructions by one or more processors causes the one or more processors to perform the additional steps of:

performing a text search to identify a plurality of textual documents;

importing all or a subset of the plurality of documents into the text viewer; and analyzing the textual documents in batch mode to identify interactions and entities to be listed in the list-based editor.

65. The computer readable medium of claim 58, wherein execution of one or more sequences of instructions by one or more processors causes the one or more processors to perform the additional steps of:

identifying aliases of at least one entity or interaction listed; and performing operations on all aliases of the at least one entity or interaction simultaneously with performance of those operations on the at least one entity or interaction.

* * * * *